United States Patent [19]
Hansen et al.

[11] Patent Number: 5,836,922
[45] Date of Patent: Nov. 17, 1998

[54] CONTAINER FOR DELIVERY OF FLOWABLE MATERIAL

[75] Inventors: Bernd Hansen, Heerstrasse 16, D-74429 Sulzbach-Laufen, Germany; Willy Leu, Reitnau, Switzerland

[73] Assignee: Bernd Hansen, Sulzbach-Laufen, Germany

[21] Appl. No.: 670,187

[22] Filed: Jun. 21, 1996

[30] Foreign Application Priority Data

Jun. 21, 1995 [DE] Germany .......................... 195 22 451.5

[51] Int. Cl.[6] .................................................. A61M 5/178
[52] U.S. Cl. ........................ 604/214; 604/216; 604/192; 604/200; 222/95; 222/541.2
[58] Field of Search ................................ 604/68, 72, 181, 604/185, 186, 187, 192, 197, 199, 200, 207–211, 212, 216, 214, 217, 218, 227, 289, 294, 295, 298, 299, 302; 222/92–94, 95, 107, 157, 210, 214, 215, 206, 325, 326, 572, 541.2

[56] References Cited

U.S. PATENT DOCUMENTS

| | | | |
|---|---|---|---|
| 1,863,785 | 6/1932 | Dickinson | 604/207 |
| 2,505,411 | 4/1950 | Kolodny et al. | 604/207 |
| 2,514,575 | 7/1950 | Hein | 604/214 |
| 2,595,493 | 5/1952 | Slaby et al. | 604/214 |
| 2,685,878 | 8/1954 | Seifert, Sr. et al. | 604/204 |
| 2,935,067 | 5/1960 | Bouet | 604/216 |
| 2,950,717 | 8/1960 | Bouet | 604/214 |
| 3,161,194 | 12/1964 | Chapman | 604/214 |
| 3,190,619 | 6/1965 | Penney et al. | 604/216 |
| 3,512,524 | 5/1970 | Drewe | 604/216 |
| 3,938,514 | 2/1976 | Boucher | 604/216 |
| 3,998,223 | 12/1976 | Dawe | 604/214 |
| 4,296,071 | 10/1981 | Weiss et al. | 604/216 |
| 4,966,312 | 10/1990 | Waring | 604/216 |
| 5,242,422 | 9/1993 | Schneberger et al. | 604/216 |
| 5,308,343 | 5/1994 | Gafner | 604/186 |
| 5,337,925 | 8/1994 | Ferrara, Jr. | 604/214 |
| 5,356,016 | 10/1994 | Wiedemann | 222/95 |
| 5,356,037 | 10/1994 | Harrold | 222/95 |
| 5,538,506 | 7/1996 | Farris et al. | 604/187 |
| 5,609,580 | 3/1997 | Kwiatkowski et al. | 604/232 |
| 5,624,057 | 4/1997 | Lifshey | 604/216 |

FOREIGN PATENT DOCUMENTS

| | | | |
|---|---|---|---|
| 0144925 | 6/1985 | European Pat. Off. | |
| 1570600 | 5/1969 | France | 222/95 |
| 7313852 | 7/1973 | Germany | |
| 7737934 | 1/1981 | Germany | |
| 3823428 | 1/1990 | Germany | |

*Primary Examiner*—Ronald Stright, Jr.
*Attorney, Agent, or Firm*—Roylance, Abrams, Berdo & Goodman, L.L.P.

[57] ABSTRACT

A container for delivery of flowable material has a plastic, deformable container body which can be compressed in its longitudinal direction and a neck of smaller diameter attached to one body end with formation of a projection. The delivery through the neck projection corresponds to the volume diminution obtained by the length reduction of the body, for quantitative regulation of the material delivered through the neck. A cup-shaped bushing has its floor engaged on a shoulder projection of the body. The bushing floor has a passage opening for the neck. A piston is slidable in the bushing until it contacts the bushing floor. An indicator arrangement makes a visible indication of the movement path of the piston in the bushing.

18 Claims, 2 Drawing Sheets

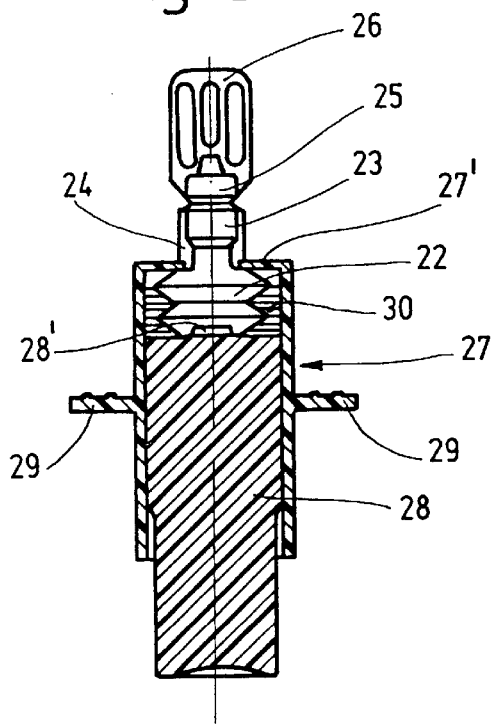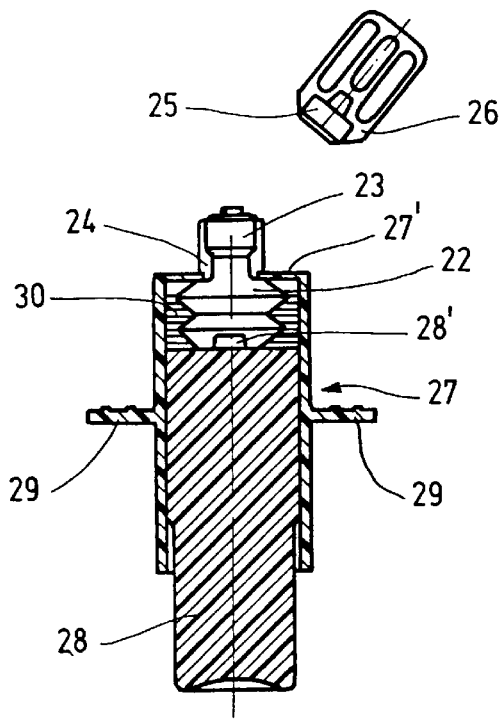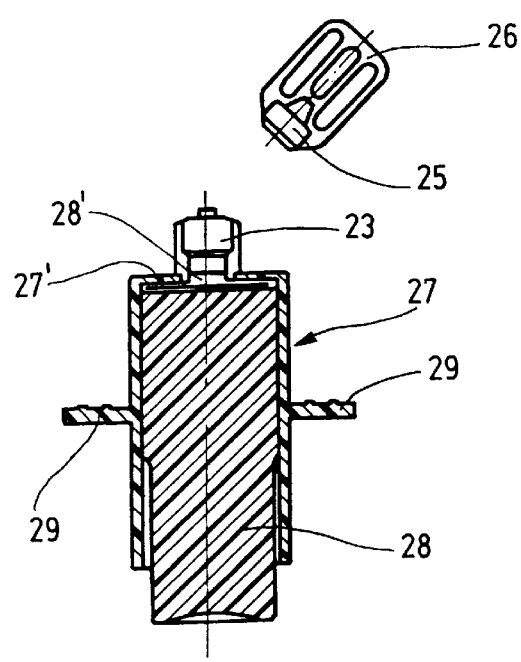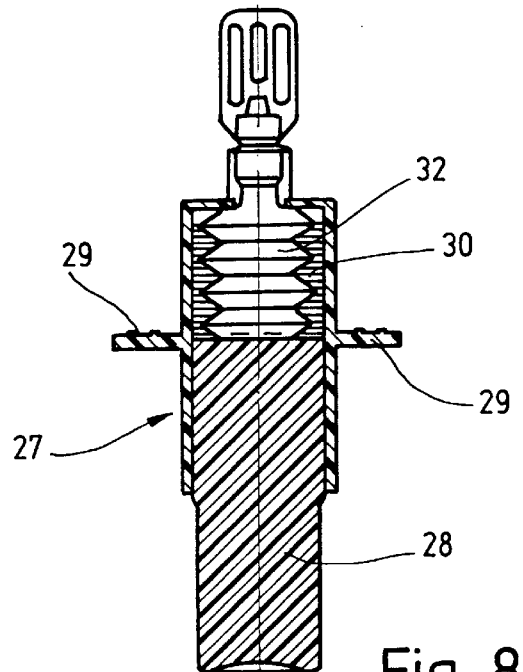

5,836,922

CONTAINER FOR DELIVERY OF FLOWABLE MATERIAL

FIELD OF THE INVENTION

The present invention relates to a device for delivery of flowable material out of a deformable plastic container. The container has a collapsible body collapsing longitudinally and a neck of smaller diameter connected to one end of the collapsible body with formation of a shoulder projection. The material is delivered through the neck in an amount corresponding to the longitudinal reduction of the body volume.

BACKGROUND OF THE INVENTION

In known containers of this type, the container is collapsible transverse to its length or along its longitudinal axis. The delivery of the material contained in the container can be quantitatively regulated only quite imprecisely.

SUMMARY OF THE INVENTION

Objects of the present invention are to provide a container which facilitates quantitatively regulated delivery or dosed delivery of the material contained in the container.

The foregoing objects are basically obtained by a container for delivery of flowable material, comprising a deformable plastic body compressible in a longitudinal direction thereof, and having a first transverse diameter and a shoulder projection. The body defines an interior volume and has an axial length. A neck is connected at one axial end of the body and has a second transverse diameter smaller than the first transverse diameter. The neck has a small projection through which flowable material is delivered. A cup-shaped bushing has a bushing floor and a passage opening in the floor receiving the neck. The floor engages the shoulder projection of the body. A piston is slidably mounted in the bushing and movable to positions in the bushing relative to the bushing floor. An indicator indicates movement of the piston in the bushing. Movement of the piston in the bushing toward the bushing floor reduces the volume of the body by reducing the axial length for regulating quantitative discharge of flowable material through the neck.

The user is not required to collapse the container directly with the fingers because the bushing is provided for this purpose. The bushing receives and holds the container body and the piston. The indicator device indicates the sliding path of this slidable piston. The container body can without difficulty be reduced in length to whatever measure is required to deliver the desired quantity of material contained in the container.

Each container body can be made commercially available in a marketable state mounted in its associated bushing. However, the container body can also be introduced into the bushing only just before delivery of its contents. The bushing and the associated piston then can be used for a plurality of similar containers.

The container can be manufactured by the blow molding or suction molding method, and can be filled and sealed shut in the mold. The device according to the present invention is thereby suitable for those materials which must be filled under sterile conditions and then must be stored until use.

An insert body of one or more parts can be inserted in the neck and/or the head. Preferably, the insertion occurs before the final formation and shaping of the part of the container receiving the insert body, in other words while the container is still located in the manufacturing mold. The inserted body can, for example, be a plug. An insert body which supports an injection needle which is not freed or exposed until separation of the head is an especially advantageous configuration. The container according to the present invention can then be used as a disposable injection needle or spraying device. Such a disposable injection needle or spraying device is of particularly low cost.

In one preferred embodiment, both the bushing and the piston are of plastic. Thus, they can be manufactured in a simple and low-cost manner.

The indicator arrangement can be graduated and have a marking arrangement cooperating with the graduation. When the container is transparent, for example, the graduation can be provided on the container and the markings can be provided on the piston. Also, the end of the piston lying in the interior of the bushing can form the markings. Alternatively, the graduation can be on the piston, and the bushing has a marking or its exposed end can be used as a marker. The indicator device, however, can also include cooperating checking elements. By means of the checking elements, the piston can be arrested by interlocking in positions within the bushing. The positions are provided along the thrust path of the piston, preferably at identical spacing from one another. These checking elements are preferably formed directly on either the bushing or the piston. For example, the piston can be provided with a projecting shoulder, and the bushing be provided with recesses or vice versa. The recesses can be in the shape of grooves, so that there are no problems with orientation.

To guarantee that only a very small quantity of contents remains in the container when the container is completely pressed together, the neck of the container should be as short as possible. Furthermore, the piston can have an axially projecting material part on its end engaging on the body. The material part presses the container floor into the interior of the container.

To be able to comfortably manipulate the device according to the present invention, a gripper can be provided. The gripper can project outward from the outside of the bushing, forming a contact surface for the index finger and the middle finger. Only the thumb is then further required for operation of the piston. This gripping arrangement can be made up of a flange built onto the bushing or two diametrically opposite arms arranged on it.

Toward the end of the delivery stage, the device can still be controlled comfortably where the length of the piston, according to one advantageous embodiment, is at least identical to the length of the bushing.

Different shapes and forms can be considered for the container. For example, a larger exterior diameter can be selected in comparison to the axial length, so that the wall forming the covering of the container need not be especially resistant to deformation. Advantageously, the container can also be in the form of a bellows.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure:

FIG. 5 is a side elevational view in partial section of a container according to a third embodiment of the present invention before use;

FIG. 6 is a side elevational view in section of the container of FIG. 5 following opening of the container and before delivery of its contents;

FIG. 7 is a side elevational view in section of the container of FIG. 5, completely emptied out; and FIG. 8 is a side elevational view in partial section of a container according to a fourth embodiment of the present invention before use.

DETAILED DESCRIPTION OF THE INVENTION

Figure 1:
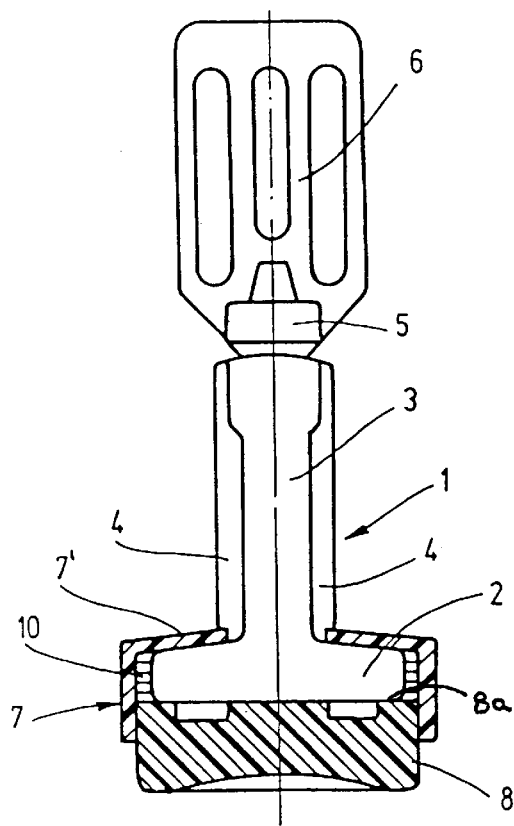
FIG. 1 is a side elevational view in partial section of a container according to a first embodiment of the present invention before use.
Figure 2:
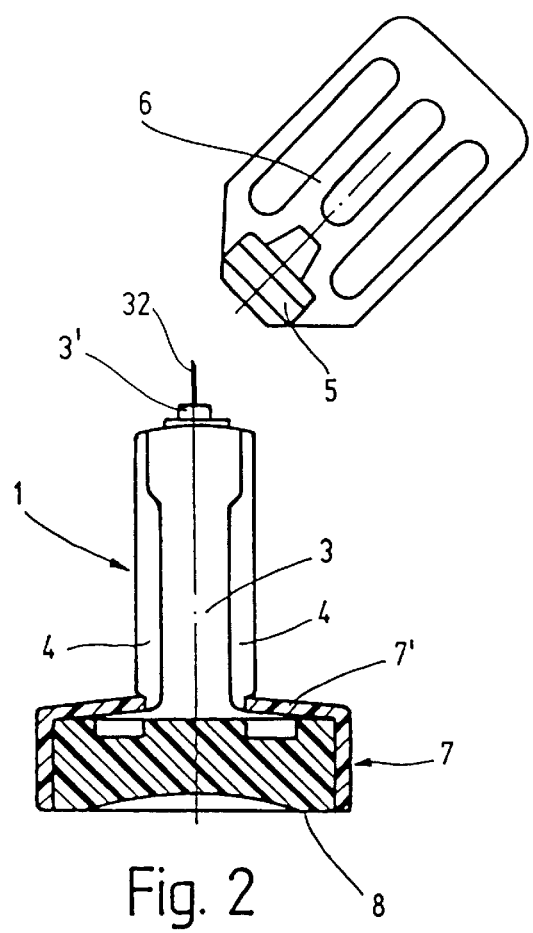
FIG. 2 is a side elevational view in partial section of the container of FIG. 1, completely emptied out.

The first embodiment of the present invention, shown in enlarged scale in FIGS. 1 and 2, includes a plastic container 1 which can also be described as an ampoule on account of its small volume. Container 1 comprises a body 2 having a transverse diameter which is some multiple greater than its axial length. A neck 3 is attached to body 2, and is reinforced by two ribs 4 arranged diametrically opposite one another constructed directly on the neck. The ribs extend the entire length of neck 3. A head 5 closes off neck 3 at the end more distant or remote from body 2.

Between a small extension 3' of reduced diameter extending from neck 3 and head 5, a narrowed down segment having reduced wall thickness for the formation of a break-off closing is provided. To be able, without difficulty, to exert the force on head 5 required for breaking off head 5 from neck 3, a flat gripping arrangement 6 is formed on head 5. The diameter of body 2 is some multiple greater than the diameter of neck 3.

The shoulder projection surface forming the transfer or connection from the outer surface of body 2 to neck 3 is practically free of slope. Furthermore, the wall forming the outer surface or side wall of body 2 is considerably thinner than that of the floor and of the shoulder projection lying opposite or facing it. The outer surface of body 2, therefore, can be deformed with a relatively small application of force to cause the floor to come into contact with the shoulder projection surface lying opposite it.

Container 1 is preferably manufactured by the blow molding method described in German Patent No. 44 39 231 or U.S. Pat. application Ser. No. 08/551,025, filed Oct. 31, 1995 now U.S. Pat. No. 5,687,550 and entitled Blow Molding Sealed Container System, the subject matter of which is hereby incorporated by reference. The container is filled in the blow mold free of air and in sterile conditions. Additionally, the container is closed in the blow mold by the formation of head 5 directly thereon. An insert body can be inserted, before the formation of small extension 3', the narrowed down segment, head 5 and gripping member 6.

Figure 3:
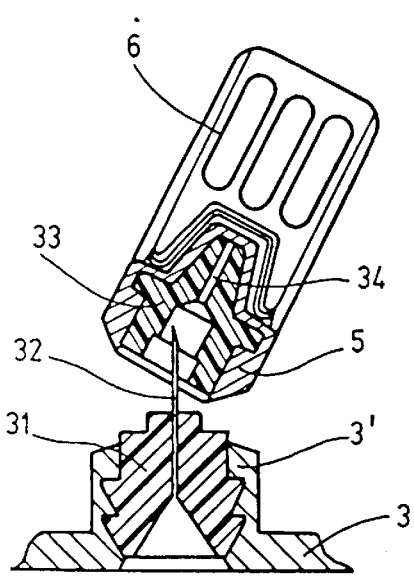
FIG. 3 is a partial side elevational view in section of the head and the neck of the container of FIGS. 1 and 2, with head removed.

A needle support insert body 31 is inserted in the small extension 3' of neck 3 in this exemplary embodiment, and carries an injection needle 32, as shown in FIG. 3. The needle extends beyond the end of needle support 31 further from neck 3. A protective body 33 is mounted on this exposed extension end, is inserted in head 5, and receives injection needle 32 in its passage 34. When head 5 is separated from small extension 3', along the break point or line of the break-off closing, protective body 33 remains connected securely with head 5, and is raised from needle carrier 31 connected securely with small extension 3'.

Container 1 is in a marketable state without being inserted in a cup-shaped bushing 7, or is inserted in a cup-shaped bushing 7 before the filling in of liquid, which in the first embodiment is a pharmaceutical preparation to be injected. The bushing floor 7' is provided with a central opening for the passage of head 5 and neck 3. An inherently stable piston 8, configured as a plastic injection or spraying part, is received in the inherently stable bushing 7. Bushing 7 is also configured as a plastic injection or spraying part. Piston 8 is guided longitudinally slidably in bushing 7, and, in the first embodiment, has an axial length equal to the axial length of container body 2.

Bushing 7 in the first embodiment is formed of transparent material. The bushing outer surface is provided with graduation 10 extending in the axial direction. The graduation is subdivided corresponding to the lowest quantity of quantitatively regulated delivery for which it has the capacity. The surrounding edge forms a marking 8a on the end of piston 8, engaging on the floor of body 2, and cooperates with this graduation arrangement.

Before removal of the material contained in container 1, head 5 is separated from small extension 3' of neck 3 along the break-off point by twisting or tilting gripping member 6 relative to neck 3. At this point the disposable injection needle is ready for use. Following the introduction of injection needle 32, piston 8 can be pressed into bushing 7 for an axial distance corresponding to the volume to be delivered. The volume variation and the delivered quantity can be read on the graduation of bushing 7 in connection with the position of the edge or marking 8a of piston 8.

Piston 8 can be manually pressed into bushing 7, using one hand only, by placing neck 3 between the index finger and the middle finger so that the thumb can be pressed against the top end of piston 8 extending out of bushing 7. Container 1 is completely emptied, except for the remainder volume found in neck 3, when the floor of body 2 engages the passage into neck 3, as shown in FIG. 2.

In addition to the graduation or instead of that graduation, bushing 7 or piston 8 can be provided with a series of annular groove-like recesses. An annular bead, formed on the other part, can be snapped into each recess in a force-locking manner. Quantitatively regulated volumes of the material corresponding to the volume variation between any two sequential grooves can then be delivered. In the first embodiment, the interior covering surface of bushing 7 is provided with annular grooves 10, arranged adjacent to one another in axial direction. An annular bead of piston 8 is caught in the grooves 10.

Figure 4:
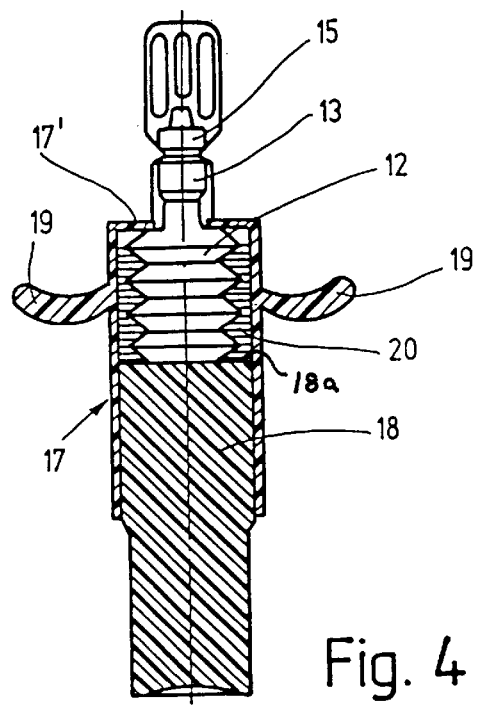
FIG. 4 is a side elevational view in partial section of a container according to a second embodiment of the present invention before use.

The second embodiment of the container shown in FIG. 4 comprises a body 12 with the configuration of a bellows. Such a body can likewise be manufactured by the blow molding method. A plastic neck 13 is formed directly on body 12 and connected to body 12 in its longitudinal direction. Neck 13 is considerably shorter than neck 3 in the first embodiment of FIGS. 1 to 3 to reduce the residual quantity remaining in neck 13 to as small a quantity as possible. Above a narrowed down break-off point or line, a head 15 is formed directly on neck 13. The manufacture of container 1, the filling of material and the sealing can occur as in the first embodiment by the blow molding method under sterile conditions. Furthermore, as in that case, a one- or multi-part insert body is inserted into neck 13 or a small extension of the neck. A part of the insert can be found in head 15.

Body 12 is arranged in a cup-shaped bushing 17. The bushing floor 17' has a central passage opening for neck 13. The interior diameter of bushing 17, the same as that of bushing 7, is at least the same magnitude larger than the exterior diameter of body 12 or 2 before diameter expansion during longitudinal reduction of the body. A piston 18, formed as a plastic injection or spraying part, is guided longitudinally slidably in the bushing 17, also formed as a plastic injection or spraying part. In this second embodiment, sufficiently great contact surface is not present for two fingers to be placed on floor 17' of bushing 17. Thus, two diametrically opposite, outwardly extending arms 19 are formed directly on the outside of bushing 17. Two fingers can be placed on arms 19, while piston 18 is pressed with the thumb into bushing 17 in a controlled manner for quantitatively regulated delivery of the material contained in the container as body 12 is reduced correspondingly in its length.

As in the first embodiment, the second embodiment has an indicator device which is not visible in FIG. 4 to indicate the path of movement of the piston in the bushing. This indicator device has a graduation. The graduation can be provided on piston 18 or on bushing 17. A marking arrangement on the other part cooperates with the graduation. However, instead of a graduation or in addition to a graduation, checking elements can be provided on bushing 17 and piston 18, for example, to provide a series of annular grooves 20 in the interior surface of bushing 17, in which a shoulder projection or means 18a formed directly on piston 18 can be arrested or engaged in form-locking states forming checking means on the bushing and piston.

The third embodiment, shown in FIGS. 5 to 7, differs from the second embodiment, by the smaller volume and therefore a shorter axial length of body 22 of its container, and by an additional radially projecting flange 29 formed directly on the outside of bushing 27 as another gripping member. Neck 23, ribs 24, head 25, and its gripping member 26 are configured exactly as in the second embodiment. For the other individual features, reference is made to the description of the other embodiments. This third embodiment can be configured as a disposable needle or spray device.

Before quantitatively regulated delivery of the material contained in body 22, head 25 is separated from neck 23 along the break-off point or line. Piston 28 is regulated with the aid of the indicator device, and is pressed into bushing 27. The axial length of body 22 is correspondingly reduced. The indicator device has annular grooves 30 arranged adjacent to one another in the interior surface of bushing 27, and an annular bead on piston 28. An axial extension 28' of piston 28 at its end engaging the floor of body 22 assures that, with complete pressing together of body 22, only an extremely small residual quantity of material is held or remains in neck 23, especially since extension 28' even penetrates somewhat into neck 23, as shown in FIG. 7. In this third embodiment, when body 22 is completely emptied, piston 28 still extends somewhat beyond the open end or bushing floor 27' of bushing 27. As shown particularly in FIG. 7, piston 28 has a reduced diameter outer segment and a relatively larger diameter segment engaging the interior wall of bushing 27. This piston structure provides a friction-biased force opposing thrusting piston 28 into bushing 27, but with a relatively small force.

The dimensions of bushing 27 and piston 28 are determined so that, as shown in FIG. 8, bushing 27 can also hold a container with a body part 32 which is considerably longer than body part 22. Bushing 27 and piston 28 are plastic injection or spraying parts and are provided with an indicator making the degree of regulated thrust of the piston clearly visible as in the other embodiments described above. An insert body is inserted and carries an injection needle for this fourth embodiment to be used as disposable needle.

While various embodiments have been chosen to illustrate the invention, it will be understood by those skilled in the art that various changes and modifications can be made therein without departing from the scope of the invention as defined in the appended claims.

What is claimed is:

1. A container for delivery of flowable material, comprising:

a deformable, one piece, unitary plastic body compressible in a longitudinal direction thereof, and having a first transverse diameter and a shoulder projection, said body defining an interior volume and having an axial length;

a neck unitarily formed with said body at one axial end of said body, said neck having a second transverse diameter smaller than said first transverse diameter, said neck having a small projection through which flowable material is delivered;

a cup-shaped, one piece bushing formed of a small unitary piece of plastic receiving said body and having a bushing floor and a passage opening in said floor receiving said neck, said floor engaging said shoulder projection of said body;

a piston formed of a single, unitary piece of plastic, slidably mounted in said bushing and movable to positions in said bushing relative to said bushing floor; and indicators on said piston and said bushing indicating movement of said piston in said bushing, said indicators including cooperating checking means on said bushing and said piston for force-locking said bushing and said piston in relative positions along a path of movement of said piston;

whereby, movement of said piston in said bushing toward said bushing floor reduces said volume of said body by reducing said axial length for regulating quantitative discharge of flowable material through said neck.

2. The container according to claim 1 wherein a gripper projects laterally from an outside surface of said bushing.

3. The container according to claim 2 wherein said gripper comprises a flange formed directly on said bushing.

4. The container according to claim 2 wherein said gripper comprises two diametrically opposite arms.

5. The container according to claim 1 wherein a head is formed directly on said neck with a break-off closing.

6. The container according to claim 5 wherein said body, said neck and said head are formed unitarily of one integral piece.

7. The container according to claim 1 wherein said indicators comprise a graduation fixed on one of said piston and said bushing and a marking cooperating with said graduation fixed on the other of said piston and said bushing.

8. The container according to claim 1 wherein one end of said piston engages on said body and has a material part projecting axially.

9. The container according to claim 1 wherein said piston has an axial length at least equal to an axial length of said bushing.

10. The container according to claim 1 wherein said body comprises a bellows.

11. The container according to claim 1 wherein said shoulder projection extends radially from said neck at a juncture of said neck and said body; and
said bushing floor has an inner surface extending radially from said passage opening and engaging said shoulder projection.

12. A container for delivery of flowable material, comprising:
a deformable bellows body compressible in a longitudinal direction thereof, formed of a single and unitary piece of plastic and having a first transverse diameter and a shoulder projection, said body defining an interior volume and having an axial length;
a neck unitarily formed with said body at one axial end of said body, said neck having a second transverse diameter smaller than said first transverse diameter, said neck having a small projection through which flowable material is delivered;
a head is unitarily formed with said neck and said body with a frangible connection between said head and said neck;
a cup-shaped bushing, formed of a single and unitary piece of plastic, receiving said body and having a bushing floor and a passage opening in said floor receiving said neck, said floor engaging said shoulder projection of said body;
a gripper unitarily formed with said bushing and projecting laterally from an outside surface of said bushing;
a piston, formed of a single and unitary piece of plastic slidably mounted in said bushing and movable to positions in said bushing relative to said bushing floor, said piston having an axial length at least equal to an axial length of said bushing; and
indicators on said piston and said bushing indicating movement of said piston in said bushing;
whereby, movement of said piston in said bushing toward said bushing floor reduces said volume of said body by reducing said axial length for regulating quantitative discharge of flowable material through said neck.

13. A container for delivery of flowable material, comprising:
a deformable, one piece, unitary plastic body compressible in a longitudinal direction thereof, and having a first transverse diameter and a shoulder projection, said body defining an interior volume and having an axial length;
a neck unitarily formed with said body at one axial end of said body, said neck having a second transverse diameter smaller than said first transverse diameter, said neck having a small projection through which flowable material is delivered;
a head formed directly on said neck with a break-off closing;
a cup-shaped, one piece, unitary bushing receiving said body and having a bushing floor and a passage opening in said floor receiving said neck, said floor engaging said shoulder projection of said body;
a piston slidably mounted in said bushing and movable to positions in said bushing relative to said bushing floor; and
indicators on said piston and said bushing indicating movement of said piston in said bushing;
whereby, movement of said piston in said bushing toward said bushing floor reduces said volume of said body by reducing said axial length for regulating quantitative discharge of flowable material through said neck.

14. A container for delivery of flowable material, comprising:
a deformable, one piece, unitary plastic body compressible in a longitudinal direction thereof, and having a first transverse diameter and a shoulder projection, said body defining an interior volume and having an axial length;
a neck unitarily formed with said body at one axial end of said body, said neck having a second transverse diameter smaller than said first transverse diameter, said neck having a small projection through which flowable material is delivered, said neck receiving an insert body, said insert body including an injection needle for use as a disposable needle;
a cup-shaped, one piece, unitary bushing receiving said body and having a bushing floor and a passage opening in said floor receiving said neck, said floor engaging said shoulder projection of said body;
a piston slidably mounted in said bushing and movable to positions in said bushing relative to said bushing floor; and
indicators on said piston and said bushing indicating movement of said piston in said bushing;
whereby, movement of said piston in said bushing toward said bushing floor reduces said volume of said body by reducing said axial length for regulating quantitative discharge of flowable material through said neck.

15. A container for delivery of flowable material, comprising:
a deformable, one piece, unitary plastic body compressible in a longitudinal direction thereof, and having a first transverse diameter and a shoulder projection, said body defining an interior volume and having an axial length;
a neck unitarily formed with said body at one axial end of said body, said neck having a second transverse diameter smaller than said first transverse diameter, said neck having a small projection through which flowable material is delivered;
a head formed directly on said neck with a break-off closing;
a cup-shaped, one piece bushing formed of a small unitary piece of plastic receiving said body and having a bushing floor and a passage opening in said floor receiving said neck, said floor engaging said shoulder projection of said body;
a piston formed of a single, unitary piece of plastic, slidably mounted in said bushing and movable to positions in said bushing relative to said bushing floor; and
indicators on said piston and said bushing indicating movement of said piston in said bushing;
whereby, movement of said piston in said bushing toward said bushing floor reduces said volume of said body by reducing said axial length for regulating quantitative discharge of flowable material through said neck.

16. The container according to claim 15 wherein
said body, said neck and said head are formed unitarily of one integral piece.

17. A container for delivery of flowable material, comprising:
- a deformable, one piece, unitary plastic body compressible in a longitudinal direction thereof, and having a first transverse diameter and a shoulder projection, said body defining an interior volume and having an axial length;
- a neck unitarily formed with said body at one axial end of said body, said neck having a second transverse diameter smaller than said first transverse diameter, said neck having a small projection through which flowable material is delivered and having an insert body therein of an injection needle for use as a disposable needle;
- a cup-shaped, one piece bushing formed of a small unitary piece of plastic receiving said body and having a bushing floor and a passage opening in said floor receiving said neck, said floor engaging said shoulder projection of said body;
- a piston formed of a single, unitary piece of plastic, slidably mounted in said bushing and movable to positions in said bushing relative to said bushing floor; and
- indicators on said piston and said bushing indicating movement of said piston in said bushing;
- whereby, movement of said piston in said bushing toward said bushing floor reduces said volume of said body by reducing said axial length for regulating quantitative discharge of flowable material through said neck.

18. The container according to claim 17 wherein
said neck receives an insert body including an injection needle for use as a disposable needle.

\* \* \* \* \*